(12) United States Patent
Oi

(10) Patent No.: US 11,565,121 B2
(45) Date of Patent: Jan. 31, 2023

(54) COMPOUND ELECTRODE-TYPE INTRACARDIAC DEFIBRILLATION CATHETER AND COMPOUND ELECTRODE-TYPE INTRACARDIAC DEFIBRILLATION CATHETER UNIT

(71) Applicants: INTER NOVA MEDICAL CO., LTD., Tokyo (JP); FUKUDA DENSHI CO., LTD., Tokyo (JP)

(72) Inventor: Takeshi Oi, Tokyo (JP)

(73) Assignee: INTER NOVA MEDICAL CO., LTD., Tokyo (JP)

( * ) Notice: Subject to any disclaimer, the term of this patent is extended or adjusted under 35 U.S.C. 154(b) by 545 days.

(21) Appl. No.: 16/497,873

(22) PCT Filed: Mar. 27, 2018

(86) PCT No.: PCT/JP2018/012417
§ 371 (c)(1),
(2) Date: Dec. 5, 2019

(87) PCT Pub. No.: WO2018/181301
PCT Pub. Date: Oct. 4, 2018

(65) Prior Publication Data
US 2020/0384276 A1 Dec. 10, 2020

(30) Foreign Application Priority Data
Mar. 28, 2017 (JP) ............................. JP2017-111185

(51) Int. Cl.
*A61N 1/05* (2006.01)
*A61N 1/39* (2006.01)
(Continued)

(52) U.S. Cl.
CPC ............ *A61N 1/3968* (2013.01); *A61L 29/06* (2013.01); *A61L 29/10* (2013.01); *A61L 29/12* (2013.01);
(Continued)

(58) Field of Classification Search
CPC ..................... A61N 1/0563; A61N 1/39–3993
See application file for complete search history.

(56) References Cited

U.S. PATENT DOCUMENTS 3,942,536 A * 3/1976 Mirowski .............. A61N 1/056
607/6
5,165,403 A * 11/1992 Mehra .................. A61N 1/3918
607/2

(Continued)

*Primary Examiner* — Eric D. Bertram
(74) *Attorney, Agent, or Firm* — Wenderoth, Lind & Ponack, L.L.P.

(57) ABSTRACT

A composite electrode intracardiac defibrillation catheter includes a first electrode group including at least two first electrodes for detecting an electrophysiological electrical signal of a site or a cell group in a heart chamber, and a second electrode group including at least one second electrode located between an adjacent pair of the at least two first electrodes for causing an electric current by a high-voltage defibrillation electric shock for defibrillation to flow in a contact site in the heart chamber or a contact site in a vein, and a conductive length of a surface of the at least one second electrode in a longitudinal direction of the composite electrode intracardiac defibrillation catheter is longer than a conductive length of each of the at least two first electrodes.

24 Claims, 14 Drawing Sheets

(51) Int. Cl.
*A61L 29/06* (2006.01)
*A61L 29/10* (2006.01)
*A61L 29/12* (2006.01)
*A61L 29/14* (2006.01)

(52) U.S. Cl.
CPC .......... *A61L 29/146* (2013.01); *A61N 1/0563* (2013.01); *A61N 2001/0585* (2013.01)

(56) References Cited

U.S. PATENT DOCUMENTS

| | | | | |
|---|---|---|---|---|
| 5,871,530 | A * | 2/1999 | Williams | A61N 1/0563 607/122 |
| 6,256,541 | B1 * | 7/2001 | Heil | A61N 1/0573 607/128 |
| 2002/0019651 | A1 * | 2/2002 | Griffin, III | A61N 1/3956 607/5 |
| 2010/0121421 | A1 * | 5/2010 | Duncan | A61N 1/05 607/116 |
| 2011/0319948 | A1 * | 12/2011 | Onodera | A61N 1/0563 607/5 |
| 2016/0158567 | A1 * | 6/2016 | Marshall | A61B 5/287 607/116 |

* cited by examiner

COMPOUND ELECTRODE-TYPE INTRACARDIAC DEFIBRILLATION CATHETER AND COMPOUND ELECTRODE-TYPE INTRACARDIAC DEFIBRILLATION CATHETER UNIT

TECHNICAL FIELD

The present invention relates to a composite electrode type intracardiac defibrillation catheter that is inserted into a heart chamber to remove atrial fibrillation and a composite electrode type intracardiac defibrillation catheter unit.

BACKGROUND ART

Conventionally, as an apparatus for removing atrial fibrillation, an external defibrillator that applies electrical stimulation from outside the body is known. However, since a large amount of electrical energy is applied from outside the body to the heart that is causing fibrillation, it is painful due to electrical stimulation and is a large burden for the patient and may cause burns to the skin. Against this background, defibrillation using an intracardiac defibrillation catheter has been proposed (for example, JP 2010-63708 A (U.S. Pat. No. 4,545,210)).

As a conventional example of an intracardiac defibrillation catheter, it will be described in JP 2010-63708 A (U.S. Pat. No. 4,545,210). First, FIG. 1 is a plan view schematically showing an example of a conventional intracardiac defibrillation catheter unit 200 that performs defibrillation. The outer shape of a catheter shaft 10 includes an EP inspection electrode group 20G in which a plurality of EP (electrophysiological) inspection electrodes 20 provided on the surface thereof are collected, and two defibrillation electrode groups 31G and 32G each in which a plurality of defibrillation electrodes 30 provided on the surface thereof are collected. The groups are separately arranged to form an electrode catheter (sometimes referred to as an electric catheter) 100. The electrode catheter 100 is configured to be able to perform EP inspection and also perform defibrillation as necessary.

The catheter shaft 10 is made of, for example, a flexible resin material such as PFA (tetrafluoroethylene perfluoroalkyl vinyl ether copolymer), and the EP inspection electrodes 20 constituting the EP inspection electrode group 20G and the defibrillation electrodes 30 constituting the defibrillation electrode groups 31G and 32G are made of metal such as stainless steel, gold, or platinum, in many cases. An inter-electrode gap 40 is provided between two adjacent defibrillation electrodes 30 and between two adjacent EP inspection electrodes 20. The surface between the two defibrillation electrode groups 31G and 32G is a part of the catheter shaft 10. The surface between the defibrillation electrode group 32G and the EP inspection electrode group 20G is also a part of the catheter shaft 10.

A conductive cable (not shown in FIG. 1) is connected to each of the EP inspection electrode 20 and the defibrillation electrode 30, and the conductive cable is embedded inside the catheter shaft 10 and connected to connector pins 25 (shown in FIG. 2) of a connection termination part 23 of the intracardiac defibrillation catheter unit 200 via the insides of a strain relief 24 and a handle 50. The connection termination part 23 is mounted with another cable connector by a latch mechanism 26 (shown in FIG. 2) and connected to a control power supply unit (not shown) including a high-voltage generating power source and an EP inspection measuring instrument through the cable.

The EP inspection electrode 20 has a cylindrical shape or an annular shape whose length in the longitudinal direction along the catheter shaft 10 is shorter than that of the defibrillation electrode 30. On the other hand, the defibrillation electrode 30 has a cylindrical shape whose length in the longitudinal direction along the catheter shaft 10 is longer than that of the EP inspection electrode 20. Since the former detects an electrophysiological electrical signal of a site or a cell group in a heart chamber, the surface area is preferably small. In contrary, when the length in the longitudinal direction is long, the spatial resolution of signal detection of the EP inspection electrode 20 is lowered, and it becomes rather difficult to specify the site in the heart chamber as the detection target. The latter requires a large surface area to flow current due to a high-voltage defibrillation electric shock for defibrillation at a contact site in the heart chamber or at contact sites in the heart chamber and veins. Therefore, the defibrillation electrode 30 employs a cylindrical shape whose length in the longitudinal direction along the catheter shaft 10 is long.

The tip portion of the catheter shaft 10 constitutes a rounded catheter shaft head 45 for easy introduction into the heart chamber through the vein percutaneously.

In order to perform defibrillation, in a site in the heart chamber where the defibrillation is occurring, the position and bending of the electrode catheter 100 in the heart chamber are changed by an operator's hand operation so that the site passes through a current path between the two defibrillation electrode groups 31G and 32G. The hand operation is performed by moving the handle 50, particularly a knob 22 connected to a grip part 21, the strain relief 24, and a pull wire (not shown) embedded in the catheter shaft 10 back and forth in the longitudinal direction of the catheter shaft 10.

By pulling the pull wire forward, the tip of the electrode catheter 100 is bent, and the electrode catheter 100 can be easily advanced into a bent portion in a venous blood vessel or a heart chamber.

Since the defibrillation electrode 30 uses only a cylindrical electrode, it is difficult to ensure a sufficient current emission area. In order to increase the current emission area, in the defibrillation electrode groups 31G and 32G, there is no choice but to reduce the inter-electrode gap 40 between the adjacent defibrillation electrodes 30 and to lengthen the length of a cylindrical shape of each of the defibrillation electrodes 30.

However, when doing this, since the defibrillation electrode 30 is made of metal, the electrode catheter 100 becomes inflexible as a whole, and it becomes difficult to bend and advance the electrode catheter 100 in the vein or the heart chamber, which makes it impossible to smoothly introduce and place the electrode catheter 100 at a specific site in the vein or heart chamber to be defibrillated. For this reason, there is a limit to increasing the current emission area of the defibrillation electrode 30. As a result, it becomes difficult to sufficiently supply the heart with a current necessary for effective defibrillation. Further, the loss of the flexibility of the electrode catheter 100 is not preferable because it causes damage to the inner wall of the vein or heart chamber by moving the electrode catheter 100 in the vein or heart chamber.

The fact that the current emission area cannot be sufficiently ensured electrically means that when the electrode catheter 100 is inserted into the heart chamber or a coronary vein, the impedance of the electrode catheter 100, when seen from the connector pins 25 connected to the defibrillation electrode groups 31G and 32G, increases. Therefore, when a high voltage is applied to the connector pins 25 connected to the defibrillation electrode groups 31G and 32G in order to perform defibrillation, between portions of the conductive cable from the connector pins 25 to the defibrillation electrodes 30, especially between portions of the conductive cable leading to the defibrillation electrode groups 31G and 32G, dielectric breakdown occurs due to high voltage. Then, the high voltage applied to the connector pins 25 is short-circuited at the dielectric breakdown portion, the energy for defibrillation is not supplied to a fibrillation occurring site or a site where a signal caused by fibrillation is generated, and defibrillation cannot be performed.

Once dielectric breakdown due to high voltage occurs, the insulation between portions of the conductive cable respectively connected to the defibrillation electrode groups 31G and 32G decreases or portions of the cable are brought into conduction, and a pinhole or a current path is irreversibly formed in the dielectric breakdown portion due to the dielectric breakdown. As a result, a defibrillation electric shock cannot be applied to the fibrillation site. Therefore, the intracardiac defibrillation catheter can no longer be used and must be replaced with a new intracardiac defibrillation catheter. In that replacement, it is necessary to perform again the operation of removing the intracardiac defibrillation catheter in use from the coronary vein, puncturing a new intracardiac defibrillation catheter, guiding and advancing it into the coronary vein. Thus, the burden on the practitioner and the physical burden on the patient will increase.

Since the EP inspection electrodes 20 are disposed behind the catheter shaft head 45 at the tip portion of the electrode catheter 100 and behind the defibrillation electrode groups 31G and 32G, even when the electrode catheter 100 is advanced into the coronary vein via the coronary sinus, it is difficult to measure the potential in the back of the coronary vein, and as a result, its function as a catheter for EP inspection is limited.

Defibrillation is performed targeting a coronary sinus generating electrical stimulation that causes arrhythmia, an atrioventricular node where electrical stimulation is adjusted, an atrial muscle or a ventricular muscle that is a site in the heart chamber that is causing fibrillation (hereinafter referred to as an "abnormal site"). That is, a DC high-voltage defibrillation electric shock is applied to the defibrillation electrode, groups 31G and 32G, the current path between the defibrillation electrode groups 31G and 32G flows to these abnormal sites, and thereby a DC high-voltage defibrillation electric shock is applied to these abnormal sites to stop generation and reentry of electrical stimulation in the abnormal portion, thus allowing normal myocardial contraction to be performed.

In the normal state of the heart, only the sinus node spontaneously produces electrical stimulation, and the electrical stimulation passes through the gap junction and is transmitted to the atrioventricular node, the atrial muscle, a His bundle, right and left leg Purkinje fibers, and the ventricle, and thereby the heart muscle contracts. However, the abnormal heart motion appears as an arrhythmia, and the main causes thereof are abnormal generation of cellular excitement and abnormal transmission of excitement.

Specifically, these cause abnormal excitement of cells (referred to as reentry) in the atrioventricular, atrioventricular node, and sinoatrial node, and further spontaneous excitement of atrial and ventricular myocytes. Actually, an electrocardiogram of each part of the heart is recorded as an inspection probe while electrical stimulation is applied, and the electrical stimulation occurring site in the coronary sinus or the like and the reentry route are examined. In a conventional intracardiac defibrillation catheter, if an abnormal site is found, in principle, the defibrillation electric shock is applied to the abnormal site so that a DC high-voltage current path between the two defibrillation electrode groups 31G and 32G penetrates the site, and stops the fibrillation.

However, for example, in the case of using the conventional intracardiac defibrillation catheter unit 200 as shown in FIG. 1, since the EP inspection electrode group 20G is separated from the defibrillation electrode groups 31G and 32G, even if an abnormal electrical stimulation occurring site is found, it is difficult to bring one of the defibrillation electrode groups 31G and 32G formed for the intracardiac defibrillation catheter unit 200 close to that site. Therefore, it is difficult to position the defibrillation electrode groups 31G and 32G so that the DC high-voltage current path caused by the defibrillation electric shock penetrates the site.

Even if the operator pulls the electrode catheter 100 within the heart chamber at hand, it is difficult to move one of the defibrillation electrode groups 31G and 32G to the site where the EP inspection electrode group 20G was present. This is because the electrode catheter 100 does not move along the catheter shaft 10 in the heart chamber, but can freely move in three dimensions. For this reason, it is difficult to reliably perform defibrillation even if an abnormal electrical stimulation occurring site is found in the EP inspection electrode 20.

As described above, in the conventional intracardiac defibrillation catheter unit 200, even if an abnormal electrical stimulation occurring site is found with the EP inspection electrode 20, it is difficult to reliably perform defibrillation by moving the electrode catheter 100 so that the site is located between two defibrillation electrode groups 31G and 32G.

Specifically, since the EP inspection electrode group 20G is separated from the defibrillation electrode groups 31G and 32G, even if an abnormal electrical stimulation occurring site is found with the EP inspection electrode group 20G, the abnormal site is only close to the EP inspection electrode group 20G and away from the defibrillation electrode groups 31G and 32G, so that it is difficult for the DC high-voltage current path to penetrate the site. Furthermore, it is more difficult to locate the abnormal site, that is, to perform positioning in the current path between two defibrillation electrode groups 31G and 32G. Therefore, it is difficult for the conventional intracardiac defibrillation catheter unit 200 to reliably perform defibrillation.

Therefore, in the conventional intracardiac defibrillation catheter unit 200, when an abnormal electrical stimulation occurring site is found with the EP inspection electrode 20, the operator employs a method of moving the defibrillation electrode groups 31G and 32G by pushing in or pulling out the intracardiac defibrillation catheter unit 200 into or from the body by the distance between the EP inspection electrode group 20G and the defibrillation electrode groups 31G and 32G on the electrode catheter 100 from the percutaneous approach port of the intracardiac defibrillation catheter unit 200 at hand, and bringing the defibrillation electrode 30 as close to the abnormal site as possible. For this purpose, a method is adopted which attaches a marker to the catheter shaft 10, visually observes before and after the movement of the marker with reference to the percutaneous approach port, moves the catheter shaft 10 so that a portion between the defibrillation electrode groups 31G and 32G is located at the position of the EP inspection electrode group 20 where the abnormal site is detected, and visually calculates the movement distance as accurate as possible.

However, since the flexible electrode catheter 100 described above has a three-dimensional degree of freedom, even a method for bringing the defibrillation electrode group 31G or 32G closer to the abnormal site in that way is still inaccurate and insufficient. On the other hand, when the flexibility of the electrode catheter 100 is limited by the pull wire, the removal movement of the intracardiac defibrillation catheter unit 200 does not necessarily move the electrode catheter inside the heart chamber or the like along its surface, and therefore the defibrillation electrode group 31G or 32G is not moved to the abnormal site. As described above, the conventional intracardiac defibrillation catheter unit 200 has a problem that locating the defibrillation electrode group 31G or 32G at the abnormal site, that is, the positioning for the abnormal site cannot be sufficiently achieved.

Thus, in the conventional intracardiac defibrillation catheter unit 200, proper positioning of the defibrillation electrode groups 31G and 32G is insufficient. Therefore, when the conventional intracardiac defibrillation catheter unit 200 is used, there is no guarantee that the high-voltage defibrillation electric shock will be applied in the shortest path between the defibrillation electrode groups 31G and 32G with respect to the site causing the fibrillation or the fibrillation part. Therefore, the defibrillation electric shock, which has a relatively high voltage compared to the optimum condition with the shortest path, has been applied to the defibrillation electrode so that a sufficient direct current due to the defibrillation electric shock can be made to flow to the abnormal site even for the far path.

Since such a relatively high voltage defibrillation electric shock is used, for example, in the atrial fibrillation, in addition to that the blood stagnates in the atrium and easily forms a thrombus, the application of a high-voltage defibrillation electric shock is likely to cause damage in the blood vessel wall and heart chamber wall, and as a result, a thrombus is easily generated. Therefore, there has been a risk of secondary myocardial infarction and cerebral infarction due to thrombus generated by these mechanisms during the operation. In particular, it has been reported that around 1% of patients who have undergone operation by the defibrillation electric shock may develop cerebral infarction.

Furthermore, the application of a relatively high voltage defibrillation electric shock is likely to cause the above-mentioned dielectric breakdown, requiring a replacement of the intracardiac defibrillation catheter unit during the operation, and there has been a problem of reliability in using the intracardiac defibrillation catheter unit.

From the above, it can be seen that the conventional intracardiac defibrillation catheter unit 200 has the following drawbacks: 1) it is difficult to supply necessary and sufficient current required for defibrillation to the abnormal site, 2) there is a risk of secondary myocardial infarction and cerebral infarction due to generation of thrombus, 3) at the same time, due to high impedance, the intracardiac defibrillation catheter 200 becomes unusable due to dielectric breakdown during use, and 4) replacement of this increases the burden on the patient.

In addition, in order to avoid the unusable state of the intracardiac defibrillation catheter unit 200 due to the generation of thrombus and dielectric breakdown, it is also necessary to increase the current emission amount from the defibrillation electrode 30 of the electrode catheter 100 when a defibrillation electric shock is applied.

SUMMARY OF INVENTION

Technical Problem

Therefore, it is an object of the present invention to provide a composite electrode type intracardiac defibrillation catheter and a composite electrode type intracardiac defibrillation catheter unit which can easily supply a current required for defibrillation from the defibrillation electrode to an abnormal electrical stimulation occurring site found with the EP inspection electrode and can reliably perform defibrillation.

In addition, it is another object of the present invention to provide a composite electrode type intracardiac defibrillation catheter and a composite electrode type intracardiac defibrillation catheter unit which can increase the emission current from the defibrillation electrode when the defibrillation electric shock is applied to a necessary and sufficient amount without losing flexibility of the defibrillation catheter.

Solution to Problem

Hereinafter, means for achieving the above objects will be described.

The EP inspection electrode group measures abnormal excitement in an atrioventricular node, a sinoatrial node, and further atrial and ventricular myocytes. Two or more EP inspection electrodes are used for the measurement, an electrical stimulation of a target site in the heart chamber is measured by the combination of the voltage between each electrode, and a site that is abnormally excited in the heart chamber is specified. On the other hand, in the defibrillation electrode group, each defibrillation electrode has a cylindrical shape so as to ensure flexibility so that the intracardiac defibrillation catheter can smoothly advance into the heart chamber, and the entire defibrillation electrode group is designed to have flexibility.

Therefore, in a composite electrode type intracardiac defibrillation catheter unit according to the present invention, a composite electrode having a configuration in which one or more defibrillation electrodes are arranged between EP inspection electrodes is employed to constitute an intracardiac defibrillation catheter. In this case, it can be said that the EP inspection electrode and the defibrillation electrode are adjacent to each other, and the BP inspection electrode group and the defibrillation electrode group are in the same position on the intracardiac defibrillation catheter.

Specifically, the composite electrode type intracardiac defibrillation catheter unit according to the present invention has the following electrode catheter structure which is a basic element invention.

That is, an electrode catheter, including: a flexible catheter shaft made of an insulating member having a substantially circular cross section; a plurality of electrodes formed on a surface of the catheter shaft; and a conductive cable connected to the electrodes and wired inside the catheter shaft, in which the plurality of electrodes include a first electrode group including two or more EP inspection electrodes (or, also referred to as first electrodes) and a second electrode group including one or more defibrillation electrodes (or, also referred to as second electrodes) in which one or more defibrillation electrodes are located at each portion between adjacent two of the EP inspection electrodes, and a conductive length of a surface of the defibrillation electrode in a longitudinal direction of the catheter shaft is longer than the conductive length of the EP inspection electrode. Here, the conductive length refers to the length of the surface of one electrode in the catheter shaft direction. For a plurality of electrodes that are electrically connected by themselves or other conductors, the total length of the plurality of electrodes in the catheter shaft direction is referred to as a conductive length.

Furthermore, the composite electrode type intracardiac defibrillation catheter unit (also simply referred to as a defibrillation catheter unit) according to the present invention has, in terms of practicality of use, a terminal connecting part that exists at one end of the electrode catheter and conductive connector pins provided in the terminal connecting part and electrically connected to portions of the conductive cable, respectively.

The EP inspection electrode can measure abnormal excitement in the atria and ventricle as two electrode pairs. Therefore, it can be said that the measurement position of the abnormal site is between the two EP inspection electrodes. On the other hand, since the position of the defibrillation electrode is the entire surface of the catheter shaft between the two EP inspection electrodes, the position of the defibrillation electrode is the position itself where the EP inspection electrodes are disposed. Further, since the defibrillation electrode is located between the two EP inspection electrodes, the EP inspection electrode and the defibrillation electrode are not separated from each other. Therefore, also as the entire electrode group, also the EP inspection electrode group and the defibrillation electrode group are not separated from each other.

The conductive cable connected to the EP inspection electrode and the defibrillation electrode is embedded inside the catheter shaft and wired to the terminal connecting part of one end of the catheter shaft and connected to the conductive connector pins that are provided in the terminal connecting part and electrically connected to the conductive cable, and the EP inspection electrode and the defibrillation electrode are electrically connected to a voltage detector and an external power source, respectively, and function as the intracardiac defibrillation catheter unit.

The configuration of arranging the defibrillation electrodes between the EP inspection electrodes is nothing other than arranging a new EP inspection electrode between the defibrillation electrodes. In other words, in the conventional intracardiac defibrillation catheter, the inter-electrode gap between two BP inspection electrodes is a dead space in which only the surface of the catheter shaft exists. In the present invention, the EP inspection electrodes are moved so as to sandwich the original defibrillation electrode, and in the present invention employing the electrode arrangement configured by such movement, the number of defibrillation electrodes does not increase. The configuration of arranging a plurality of defibrillation electrodes may be a configuration of adding and arranging EP inspection electrodes in the front row and the rearmost portion of the arrangement.

Adding and arranging EP inspection electrodes at the front and rearmost portions increases the number of EP inspection electrodes. However, the length of the EP inspection electrode with respect to the catheter shaft length is smaller than that of the defibrillation electrode, and the overall length of the electrode with respect to the longitudinal direction of the electrode catheter hardly changes. Therefore, even with such an electrode arrangement, the present invention does not deteriorate the flexibility as an electrode catheter.

Note that, the present invention employs an electrode arrangement in which one or more defibrillation electrodes are basically arranged between two EP inspection electrodes, but a defibrillation electrode may be further arranged at the final position of the arrangement.

FIGS. 3(A), 3(B), 3(C), and 3(D) are diagrams showing the emission of current from the defibrillation electrode. FIGS. 3(A), 3(B), 3(C), and 3(D) all show the appearance of the defibrillation electrode as viewed in the longitudinal direction, which is disposed on the surface of the catheter shaft 10. In FIGS. 3(A) and 3(B), the defibrillation electrode 30 is wound around the surface of the catheter shaft 10 and disposed. On the other hand, in FIGS. 3(C) and 3(D), the defibrillation electrode 30 is embedded in the catheter shaft 10, and the surface of the defibrillation electrode 30 and the surface of the catheter shaft 10 are coincident. As shown in FIGS. 3(A) and 3(C), in the current emission from the defibrillation electrode 30, at the end of the defibrillation electrode 30, the current is emitted toward a whole space where the defibrillation electrode 30 does not exist. This is a result derived from divE=J, which is Gauss's theorem for current, div is a mathematical operator meaning divergence, E is an electric field vector, and J is a current density vector.

From this Gauss's theorem, at the end of the defibrillation electrode 30, the emitted current goes to the whole space where the defibrillation electrode 30 does not exist, and as a result, the current emission is larger compared with the central portion of the defibrillation electrode 30 where the defibrillation electrode 30 that is itself exists in the vicinity. Therefore, as shown in FIGS. 3(B) and 3(D), at the end of the defibrillation electrode 30, the current density of the emission current is greater than that at the central portion.

The difference in the current density of the emission current seen in FIGS. 3(B) and 3(D) depends on the difference between whether the defibrillation electrode 30 protrudes from the surface of the catheter shaft 10 and whether the surface of the defibrillation electrode 30 coincides with the surface of the catheter shaft 10. In the former, since the blood space seen from the end of the defibrillation electrode 30 and the cell space on the inner surface of the heart chamber are larger than the latter, current emission is larger than that of the latter according to Gauss's theorem.

Furthermore, there is a contact resistance between the surface of the defibrillation electrode 30 and the blood or cells on the inner surface of the heart chamber that are in contact therewith, and by this effect, current emission is suppressed at the central portion of the defibrillation electrode 30 and is less likely to be suppressed at the peripheral portion than at the central portion. As a result, due to the action of contact resistance in addition to Gauss's theorem, the current density of the emission current is relatively greater at the end of the defibrillation electrode 30 than at the center of the defibrillation electrode 30, so that the current emission is even greater. Hereinafter, such an increase in current emission at the end of the defibrillation electrode 30 is referred to as a "termination effect" of the defibrillation electrode 30.

FIGS. 4(A) and 4(B) show examples of current increase due to the termination effect. This shows the effect of increase of the emission current by increase of the number of both ends of the defibrillation electrode. In FIG. 4(B), one defibrillation electrode 30 in FIG. 4(A) is divided to form two defibrillation electrodes 31a and 31b. In this division, the length in the longitudinal direction of the catheter shaft 10 including the inter-electrode gap 11 on the catheter shaft 10 and the two defibrillation electrodes 31a and 31b is the same as the length in the longitudinal direction of one defibrillation electrode 30 shown in FIG. 4(A). Accordingly, the sum of the electrode areas of the two divided defibrillation electrodes 31*a* and 31*b* is smaller than the electrode area of the defibrillation electrode 30 that is not divided.

The current density of the emission current on the surfaces of the defibrillation electrodes 30, 31*a* and 31*b* has the suspension bridge type distribution described above. In the case of arrangement of the defibrillation electrode divided into two shown in FIG. 4(B), there is no current emission from the inter-electrode gap 11. In the single defibrillation electrode arrangement shown in FIG. 4(A), the amount of current I1 emitted from a portion of the defibrillation electrode 30 corresponding to the inter-electrode gap 11 is the hatched portion shown in FIG. 4(A). The portion of the defibrillation electrode 30 corresponding to the inter-electrode gap 11 is the central portion of the defibrillation electrode 30, so this amount of current I1 is small compared to the total current emitted from the defibrillation electrode 30.

On the other hand, in the case of arrangement of the defibrillation electrode divided into two shown in FIG. 4(B) (that is, defibrillation electrodes 31*a* and 31*b*), the distribution of the emission current from the surface of each defibrillation electrode 31*a* and 31*b* is, as shown in FIG. 4(B), a suspension bridge type distribution similar to FIG. 4(A). However, in the divided defibrillation electrodes 31*a* and 31*b* shown in FIG. 4(B), from the inter-electrode gap 11, there is no current emission I1 from the portion corresponding to the inter-electrode gap 11 seen when the defibrillation electrode is not divided. However, at the new termination of the defibrillation electrode 31*a* or 31*b* formed by the division, the termination effect acts on the current emission, and the current emission at the new termination of the defibrillation electrode 31*a* or 31*b* is almost the same as the distribution of the emission current at the left and right ends of the defibrillation electrode 30 (FIG. 4(A)) having a shape not divided.

Assuming that the current amounts at the new ends formed by division of the defibrillation electrodes 31*a* and 31*b* are I2 and I3, from the comparison of FIGS. 4(A) and 4(B), the change in emission current resulting from dividing the defibrillation electrode 30 into two is I2+I3−I1. From the difference in current density shown in FIGS. 4(A) and 4(B), this change is clearly positive. This means that the defibrillation electrode by the defibrillation electrode 31*a* and the defibrillation electrode 31*b*, which are obtained by dividing one defibrillation electrode 30 into two, has a higher current emission effect than the defibrillation electrode array by one defibrillation electrode 30. In the present specification, this is referred to as an effect of increasing current emission by division. Since the essential cause is the above-mentioned termination effect, it is also referred to as an increase in current emission due to termination effect.

The effect of the increase in current emission by the above division is that, when viewed from another point of view, if the defibrillation electrode has a cylindrical shape, the total length of the divided defibrillation electrodes 31*a* and 31*b* along the catheter shaft 10 is smaller than the length of the corresponding undivided defibrillation electrode 30 along the catheter shaft 10. Then, the electrode catheter using the divided defibrillation electrodes 31*a* and 31*b* is more flexible. This is because the inter-electrode gap 11 having flexibility is included and the length of the individual defibrillation electrodes 31*a* and 31*b* each having a cylindrical shape along the catheter shaft 10 is small.

As a result of the above, since dividing the defibrillation electrode exerts a terminal effect and increases current emission, a desirable effect of avoiding generation of thrombus and dielectric breakdown of the electrode catheter using a relatively low defibrillation electric shock and of improving flexibility is produced as an intracardiac defibrillation catheter.

Specific configurations in which the defibrillation electrode according to the present invention is divided into two or more are as follows. That is, the defibrillation catheter unit includes: a flexible cylindrical member (catheter shaft) made of an insulating member having a substantially circular cross section, a first electrode group including two or more first electrodes (EP inspection electrodes) formed on the surface of the cylindrical member; a second electrode group including two or more second electrodes (defibrillation electrodes) formed on the surface of the cylindrical member and positioned between one pair of the first electrodes and each having a conductive length in the longitudinal direction of the cylindrical member equal to or longer than the conductive length in the first electrode; an electrode catheter formed of a conductive cable connected to the first electrode and the second electrode and wired inside the cylindrical member; a terminal connecting part existing at one terminal of the electrode catheter; and conductive connector pins provided at the terminal connecting part and electrically connected to the conductive cable.

Making the defibrillation catheter unit, particularly the electrode catheter, increase the current emission due to the termination effect can increase a sufficient defibrillation effect even if the applied defibrillation electric shock is relatively low. The increase in current emission due to the termination effect depends on the physical peripheral shape of defibrillation electrode and the number of defibrillation electrodes. Thus, there are also other ways to create termination effects, some of which are given in embodiments described below.

In addition to the above, another means can be used as a method of increasing the amount of current applied to the fibrillation site or the like by the defibrillation electric shock. Specifically, the means uses the EP inspection electrode, and when applying the defibrillation electric shock, applies it not only through the defibrillation electrode but also through the EP inspection electrode. Since the electrophysiological inspection in the vein or heart chamber by the EP inspection electrode is not performed when the defibrillation electric shock is applied, the EP inspection electrode is not used during this period.

Therefore, when the defibrillation electric shock is applied, in addition to the defibrillation electrode, the EP inspection electrode is also used as the application electrode. In other words, the EP inspection electrode is used in time division and used as it is as the EP inspection electrode in the electrophysiological inspection that is performed when the defibrillation electric shock is not applied, and when the defibrillation electric shock is applied, the EP inspection electrode is also used as an application electrode in addition to the defibrillation electrode.

Such time division use is possible because the feature of the electrode arrangement of the present invention that the EP inspection electrode group coexists in the same place as the defibrillation electrode group can be used as it is. In the present invention, this time division use increases the utilization efficiency of the electrode.

Advantageous Effects of Invention

In conventional intracardiac defibrillation catheters, the EP inspection electrode group is separated from the defibrillation electrode group, and thus, even if an abnormal electrical stimulation occurring site is found, it is difficult to accurately bring the defibrillation electrode group close to that site, and therefore it is difficult to cause a DC high-voltage current path to penetrate the site.

In contrast, in the intracardiac defibrillation composite electrode type catheter unit according to the present invention, the inspection electrode and the defibrillation electrode are not separated, and the EP inspection electrode group and the defibrillation electrode group are also not separated. Therefore, it is possible to allow a current to flow from the defibrillation electrode group so that the DC high-voltage current path accurately passes through the abnormal electrical stimulation occurring site found with the EP inspection electrode. As a result, defibrillation can be reliably performed.

In addition, since it is possible to allow a current to flow through such an abnormal site so that a high-voltage voltage current path accurately passes through the defibrillation electrode group, it is no longer necessary to pass a wasteful current through a site that is not effective for fibrillation, in other words, a site where fibrillation is not generated, or not an abnormal site that causes fibrillation but a site that is not effective for defibrillation. Therefore, the applied high voltage may be a voltage sufficient to supply the necessary current, the dielectric breakdown becomes difficult to cause between wirings of the conductive cable, and the electrode catheter is hardly disabled due to dielectric breakdown during use. Therefore, there is no accident of replacing the intracardiac defibrillation catheter unit during the operation, and the burden on the patient caused by such replacement is almost eliminated. As a result, defibrillation can be performed reliably and safely.

Further, in the present invention, the defibrillation electrode is divided or formed into a shape corresponding to this to exert a termination effect and increase current emission, and thereby a low-voltage defibrillation electric shock can be used. Therefore, as an intracardiac defibrillation catheter unit that avoids generation of thrombus and dielectric breakdown of the electrode catheter, and improves flexibility by dividing the defibrillation electrode or forming it into a shape corresponding thereto, it provides features and effects that contribute to performing a safe and reliable operation.

Furthermore, in the present invention, when the EP inspection electrode is used in time division and the defibrillation electric shock is applied, the EP inspection electrode also can be used for the application of the defibrillation electric shock together with the defibrillation electrode. By using the EP inspection electrode in time division like this, current emission due to defibrillation electric shock can be increased without causing a change in the shape of the electrode catheter and a change in flexibility associated therewith. As a result, the current emission can be further increased. Therefore, it is possible to use a lower-voltage defibrillation electric shock, and as an intracardiac defibrillation catheter that improves the flexibility while avoiding the generation of thrombus and dielectric breakdown of the electrode catheter, it can contribute to performing a further safe and reliable operation.

BRIEF DESCRIPTION OF DRAWINGS

FIG. 13(A) shows a temporal change in the connection destination of a first electric cable. FIG. 13(B) shows a temporal change in the operation of the EP inspection measuring instrument, and FIG. 13(C) shows a timing of application of the defibrillation electric shock for a relay.

DESCRIPTION OF EMBODIMENTS

Embodiments of the present invention will be described below with reference to the drawings.

First Embodiment

Figure 1:
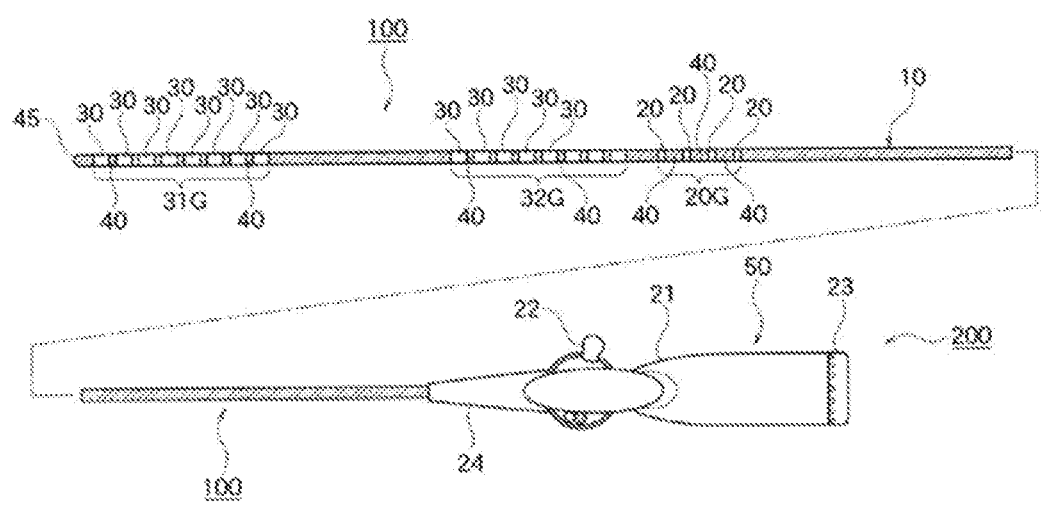
FIG. 1 is a plan view schematically showing a conventional intracardiac defibrillation catheter unit.
Figure 2:
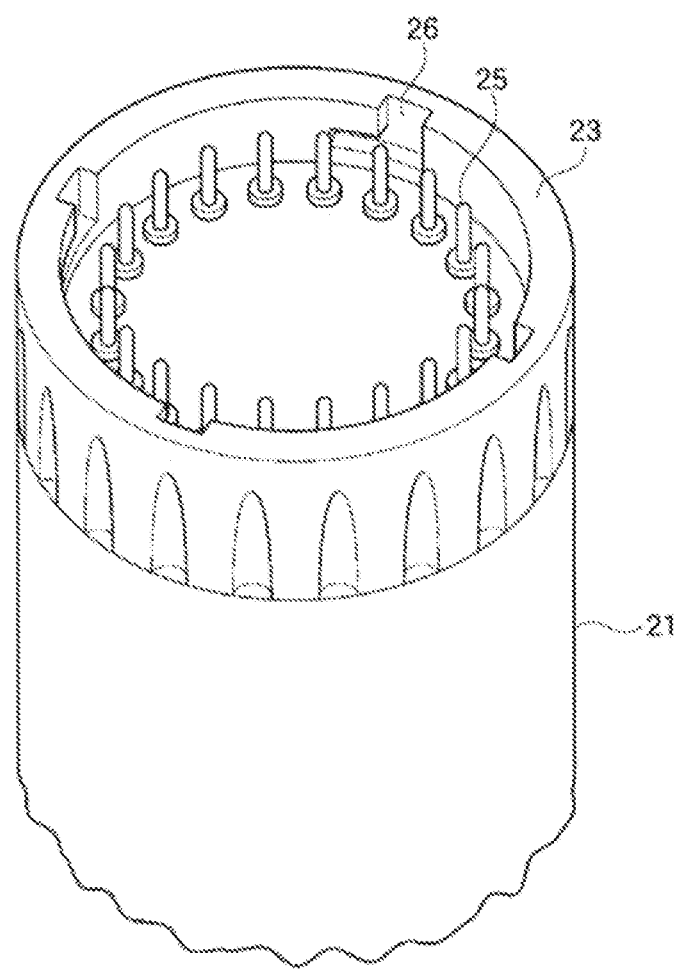
FIG. 2 is a perspective view showing a portion related to a terminal connecting part of a conventional intracardiac defibrillation catheter unit.
Figure 3:
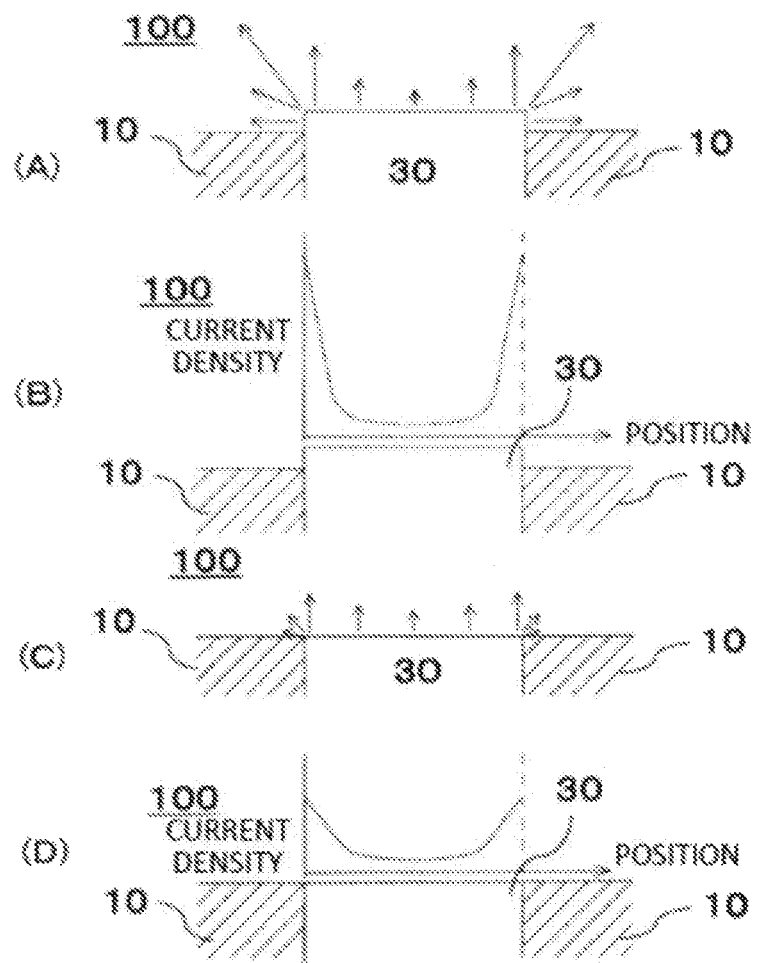
FIGS. 3(A) and 3(C) are diagrams each showing a state of current emission on the surface of a defibrillation electrode.
FIGS. 3(B) and 3(D) are diagrams each showing a magnitude of an emission current distribution on the surface of the defibrillation electrode.
Figure 4:
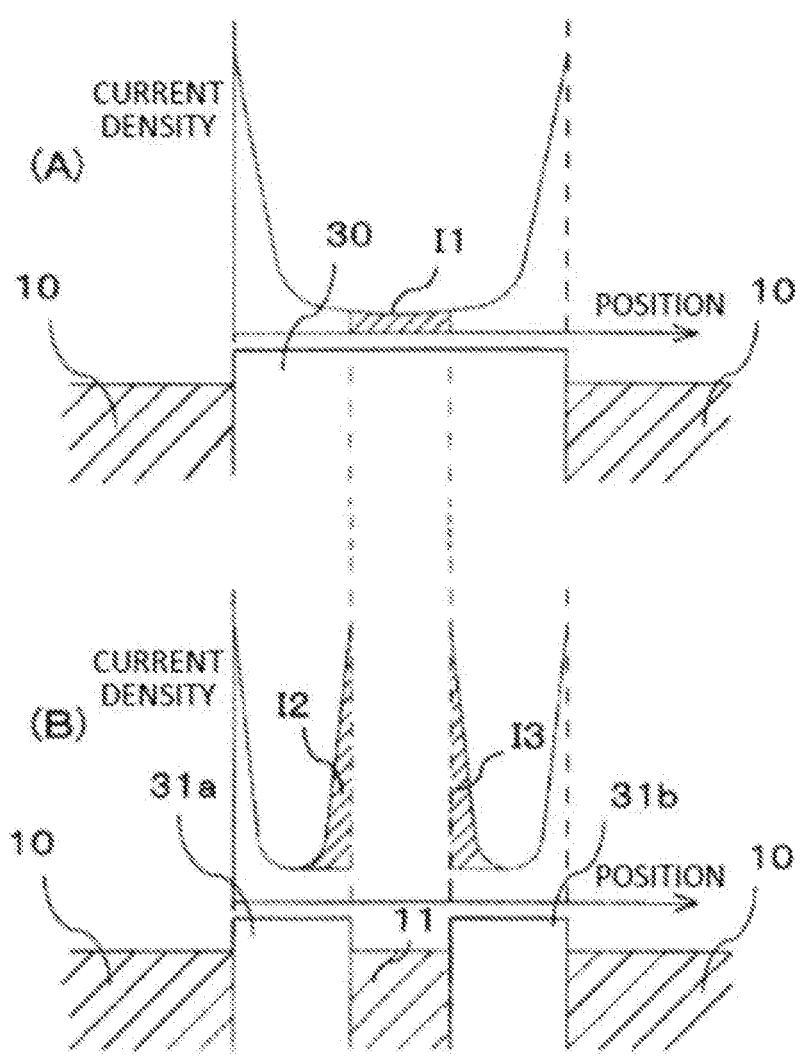
FIG. 4(A) is a diagram showing a magnitude of an emission current distribution of the defibrillation electrode.
FIG. 4(B) is a diagram showing a magnitude of an emission current when the defibrillation electrode is divided into two defibrillation electrodes.
Figure 5:
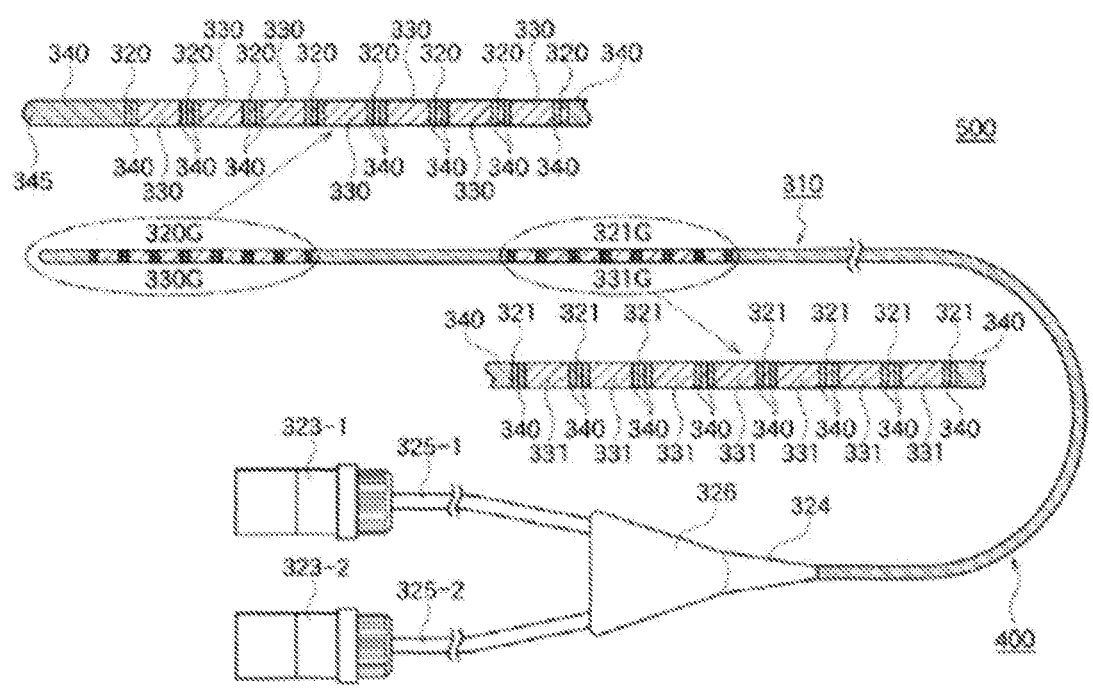
FIG. 5 is a perspective view schematically showing a composite electrode type intracardiac defibrillation catheter unit according to a first embodiment.

FIG. 5 is an overall view of a composite electrode type intracardiac defibrillation catheter unit 500 according to the first embodiment of the present invention. A composite electrode type intracardiac defibrillation catheter (also referred to simply as an electrode catheter) 400 of the composite electrode type intracardiac defibrillation catheter unit 500 is inserted percutaneously from the femoral vein or brachial vein, and reaches the atrium, ventricle and the coronary vein. Therefore, the electrode catheter 400 is long, and its main part is shown in FIG. 5. Externally, a catheter shaft 310 and a plurality of EP (electrophysiological) inspection electrodes 320 and 321 collected and provided on the surface thereof to constitute EP inspection electrode groups 320G and 321G are arranged separately on the surface of the catheter shaft 310. Defibrillation electrode groups 330G and 331G respectively including a plurality of collected defibrillation electrodes 330 and 331 are also separately arranged on the surface of the catheter shaft 310. In the figure, 340 is an inter-electrode gap.

The main part of the composite electrode type intracardiac defibrillation catheter 400 includes the catheter shaft 310, the EP inspection electrode groups 320G and 321G and the defibrillation electrode groups 330G and 331G provided on the surface thereof, the inter-electrode gap 340 therebetween, and further, a conductive cable (not shown in FIG. 5) connected to the EP inspection electrode groups 320G and 321G and the defibrillation electrode groups 330G and 331G and wired inside the catheter shaft 310. The tip portion of the catheter shaft 310 forms a rounded catheter shaft head 345.

Regarding the electrode arrangement in which the EP inspection electrode groups 320G and 321G and the defibrillation electrode groups 330G and 331G are combined, the number of the EP inspection electrodes 320 and 321 is 16 and the number of the defibrillation electrodes 330 and 331 is 14 in the present, embodiment. The number may be a minimum of two for each of the EP inspection electrodes 320 and 321 and one for each of the defibrillation electrodes 330 and 331.

Figure 6:
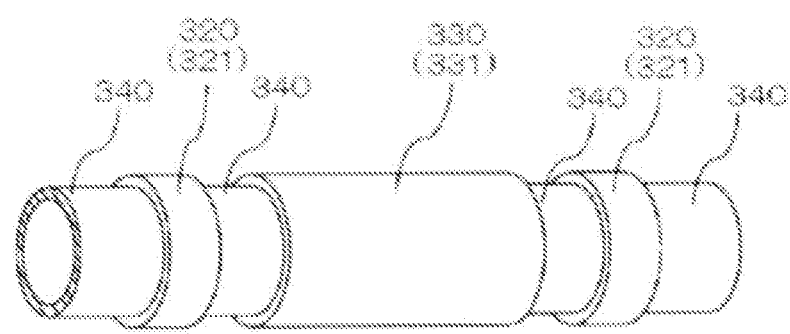
FIG. 6 is a perspective view showing main parts of an EP inspection electrode and a defibrillation electrode according to the first embodiment.

FIG. 6 takes out and shows a part of the defibrillation electrode 330 and the EP inspection electrodes 320. Since the same applies to the defibrillation electrode 331 and the EP inspection electrodes 321, the defibrillation electrode 330 and the EP inspection electrodes 320 will be described below. The defibrillation electrode 330 has a longer conductive length in the longitudinal direction of the catheter shaft 310 than the EP inspection electrode 320. The defibrillation electrode 330 is disposed between one pair of the EP inspection electrodes 320 on the catheter shaft 310, and an electrode gap 340 exists between the defibrillation electrode 330 and the inspection electrode 320. The electrode gap 340 is a part of the surface of the catheter shaft 310.

Due to the arrangement of the defibrillation electrode 330 and the EP inspection electrodes 320, both electrodes are arranged in a so-called nested manner. Therefore, assuming that there is an abnormal electrical stimulation occurring site that causes fibrillation between a pair of EP inspection electrodes 320 formed by any two adjacent EP inspection electrodes 320 of the EP inspection electrode group 320G, when it is found by detection of a voltage signal between the pair of EP inspection electrodes 320, if a DC defibrillation electric shock is applied between the two defibrillation electrode groups 330G and 331G on the spot, its current path passes through the defibrillation electrode group 330G nested with the EP inspection electrode group 320G, so that it always passes through the abnormal electrical stimulation occurring site. Therefore, a current always flows through the defibrillation electrode group 330G to the abnormal electrical stimulation occurring site, and defibrillation by the defibrillation electric shock is performed reliably. When an abnormal electrical stimulation occurring site is found with the EP inspection electrode group 321G, a current always flows through the defibrillation electrode group 331G to the abnormal electrical stimulation occurring site, and similarly, defibrillation can be performed reliably.

Inside the catheter shaft 310, conductive cables individually connected to all EP inspection electrodes 320 and 321 of the EP inspection electrode groups 320G and 321G and all defibrillation electrodes 330 and 331 of the defibrillation electrode groups 330G and 331G are embedded and connected to a control power supply unit (not shown in FIG. 5) via the strain relief 324 and the gripping part 326, through the external electric wires 325-1 and 321-2, and further by the connectors 323-1 and 323-2.

Since a large voltage is applied to the defibrillation electrodes 330 and 331 belonging to the defibrillation electrode groups 330G and 331G, dielectric breakdown is likely to occur between portions of the conductive cable reaching the defibrillation electrodes 330 and 331, respectively. Therefore, the defibrillation electrodes 330 and 331 belonging to the defibrillation electrode groups 330G and 331G are connected to the connectors 323-1 and 323-2, respectively, and the portions of the conductive cable connected to the defibrillation electrodes 330 and 331 are configured so that they are electrically separated from each other as much as possible to hardly cause dielectric breakdown inside the catheter shaft 310.

In order to embed the conductive cable connected to the defibrillation electrodes 330 and 331 and EP inspection electrode groups 320 and 321, a tube having a hollow tube shape, a porous tube called a lumen tube, or the one equivalent to these is used inside the catheter shaft 310. For the hollow tube or lumen tube, a highly insulating and flexible resin material such as tetrafluoroethylene perfluoroalkyl vinyl ether copolymer (PFA) or polytetrafluoroethylene (PTFE) is used.

The inside of the catheter shaft 310 has its inner wall layer lined with a braid of a low hardness nylon elastomer, a high hardness nylon elastomer, or a stainless steel element wire, and such a composite structure allows the flexibility of the entire catheter shaft to be suitable for close proximity to electrically abnormal excited parts to be operated.

Further, when a lumen tube is used for the catheter shaft 310, its inner wall is lined with a fluororesin layer, for example, the one made of a highly insulating material, such as tetrafluoroethylene perfluoroalkyl vinyl ether copolymer (PFA) or polytetrafluoroethylene (PTFE), and thereby it is also possible to improve the insulation between the lumen compartments.

Examples of the covering of the conductive cable include polyimide resin, polyamide resin, and polyamideimide resin. The thickness of the insulating tube is preferably 20 to 40 μm. Examples of the outer insulating material of the external electric wires 325-1 and 325-2 in which a plurality of insulating tubes are bundled include nylon elastomers such as "Pebax" (registered trademark of ARKEMA).

Second Embodiment

Figure 7:
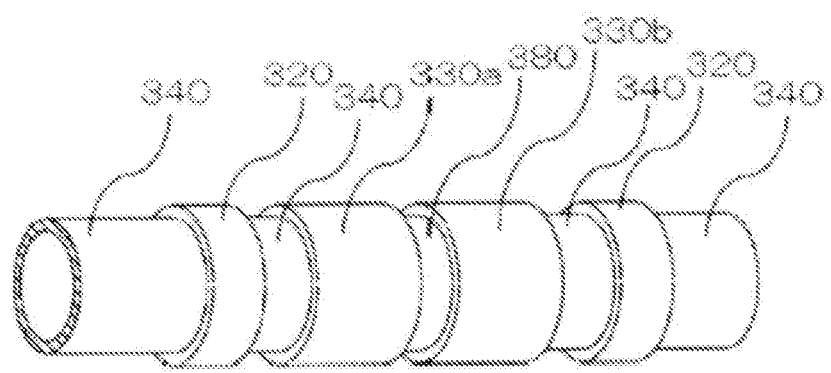
FIG. 7 is a perspective view showing main parts of an EP inspection electrode and a defibrillation electrode when a defibrillation electrode according to a second embodiment is divided.

A second embodiment is another embodiment of the composite electrode type intracardiac defibrillation catheter according to the present invention. The second embodiment has the same overall shape as the first embodiment, but differs in the configuration of the defibrillation electrode. FIG. 7 takes out and shows a part of defibrillation electrodes 330a and 330b and the EP inspection electrode 320 of the composite electrode type intracardiac defibrillation catheter according to the second embodiment. In this embodiment, the defibrillation electrode between a pair of EP inspection electrodes 320 is divided into two to form the defibrillation electrodes 330a and 330b, and an inter-electrode gap 380 is provided between the divided electrodes. The inter-electrode gap 380 is a part of the surface of the catheter shaft 310.

The total length in the longitudinal direction of the catheter shaft 310 of the two defibrillation electrodes 330a and 330b is smaller than the length in the longitudinal direction of the catheter shaft 310 of the defibrillation electrode 330 according to the first embodiment. Since the defibrillation electrodes 330a and 330b are made of a cylindrical metal, the electrode catheter of the second embodiment having a relatively small length is superior in flexibility to the electrode catheter according to the first embodiment. Further, the emission current is larger than that of the defibrillation electrode 330 of the first embodiment due to the termination effect of the defibrillation electrode.

In the second embodiment, the defibrillation electrode is divided into two, but by dividing the defibrillation electrode into three or more, it is possible to increase the emission current by the termination effect of the defibrillation electrode as in the case of dividing it into two.

Third Embodiment

Figure 8:
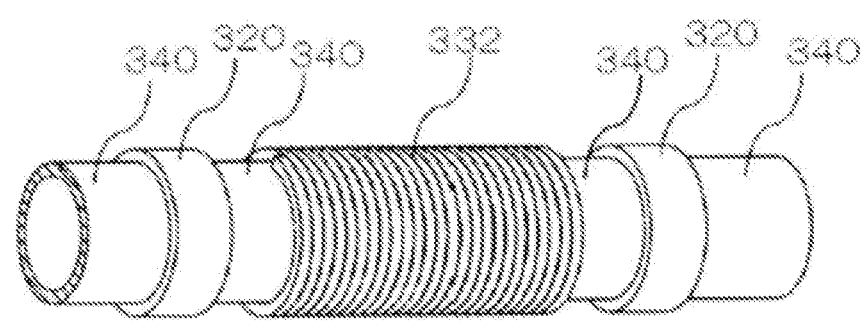
FIG. 8A is a perspective view showing main parts of an EP inspection electrode and a defibrillation electrode when a defibrillation electrode according to a third embodiment is constituted by a cylindrical spring.
FIG. 8B is a perspective view showing main parts of the EP inspection electrode and the defibrillation electrode when the defibrillation electrode according to the third embodiment is constituted by a cylindrical spring.
Figure 8:
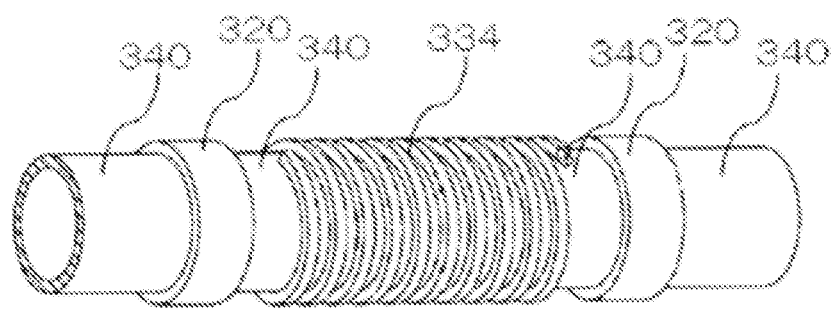

A third embodiment is still another embodiment of the composite electrode type intracardiac defibrillation catheter unit according to the present invention. The third embodiment has the same overall shape as the first embodiment, but differs in the configuration of the defibrillation electrode. FIG. 8A takes out and shows a part of a defibrillation electrode 332 and the EP inspection electrode 320 of the composite intracardiac defibrillation catheter according to the third embodiment.

Here, the defibrillation electrode 332 is a spiral-shaped electrode wound around the surface of the catheter shaft 310. This spiral-shaped electrode can be formed by rotating and cutting a cylindrical metal electrode using a laser processing machine and providing a separation slit that spirals on the surface. Alternatively, a strip-shaped metal plate having a rectangular cross section can be also formed in a spiral shape so that its inner diameter is substantially the same as the outer diameter of the catheter shaft 310. In the spiral-shaped defibrillation electrode 332, the cut portion of the separation slit or the edge of the spiral exhibits a termination effect, and the emission current is larger than that of the defibrillation electrode 330 of the first embodiment and that of the defibrillation electrodes 330a and 330b of the second embodiment.

In particular, in the third embodiment, the defibrillation electrode 332 is a spiral-shaped electrode wound around the surface of the catheter shaft 310, but the spiral of the defibrillation electrode 332 is densely wound. That is, the fibrillation electrode 332 is formed by being wound around the surface of the catheter shaft 310 such that portions of the fibrillation electrode 332 are in contact with each other at the separation slit of the spiral. Alternatively, in other words, it can be said that the spiral interval of the spiral shape of the defibrillation electrode 332 is dense.

Furthermore, since the defibrillation electrode 332 is a spiral shape and no longer a cylindrical shape if attention is paid to the portion, the flexibility in the longitudinal direction of the catheter shaft 310 is superior to that of the electrode catheter in the first and second embodiments where the defibrillation electrode has a cylindrical shape.

Fourth Embodiment

A fourth embodiment is still another embodiment of the composite electrode type intracardiac defibrillation catheter unit according to the present invention. The fourth embodiment has the same overall shape as the first embodiment, but differs in the configuration of the defibrillation electrode. FIG. 8B takes out and shows a part of a defibrillation electrode 334 and the EP inspection electrode 320 of the composite electrode type intracardiac defibrillation catheter according to the fourth embodiment. The defibrillation electrode 334 is a spiral-shaped electrode wound around the surface of the catheter shaft 310 as in the defibrillation electrode 332 according to the third embodiment.

In the third embodiment, the spiral of the defibrillation electrode 332 is densely wound, but in the fourth embodiment, the spiral of the defibrillation electrode 334 is roughly wound. That is, the fibrillation electrode 332 is formed by being wound around the surface of the catheter shaft 310 such that portions of the fibrillation electrode are not in contact with each other at the separation slit of the spiral. Alternatively, in other words, it can be said that the spiral interval of the spiral shape of the defibrillation electrode 334 is rough. In the present embodiment, because of the rough winding, the termination effect is larger than that of the dense winding, but the number of terminations is smaller than that of the dense winding, and the conductive length of the defibrillation electrode 334 is also smaller than that of the defibrillation electrode 332 of the third embodiment.

However, compared with the densely wound spiral-shaped defibrillation electrode 332, the roughly wound spiral-shaped defibrillation electrode 334 has a larger space to be seen from the end portion thereof, so that the increase in current emission due to the termination effect is large, and the total emission current is larger than the emission current in the third embodiment using the densely wound spiral-shaped defibrillation electrode 332. Of course, the emission current in the present fourth embodiment is larger than that in the first embodiment using the defibrillation electrode 330 and that in the second embodiment using the defibrillation electrodes 330a and 330b.

Fifth Embodiment

Figure 9:
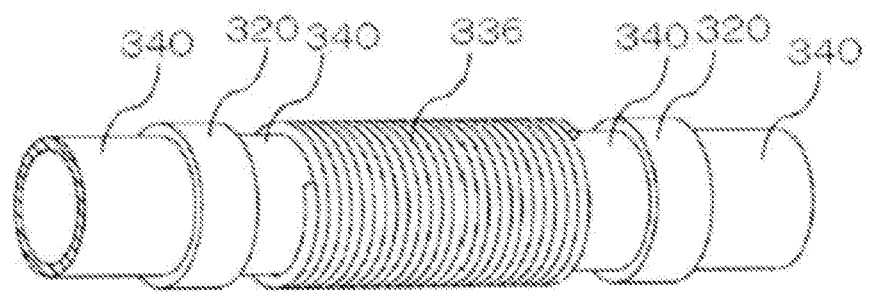
FIG. 9A is a perspective view showing main parts of an EP inspection electrode and a defibrillation electrode when a defibrillation electrode according to a fifth embodiment is constituted by a circular single wire cable.
FIG. 9B is a perspective view showing main parts of an EP inspection electrode and a defibrillation electrode when a defibrillation electrode according to a sixth embodiment is constituted by a circular single wire cable.
Figure 9:
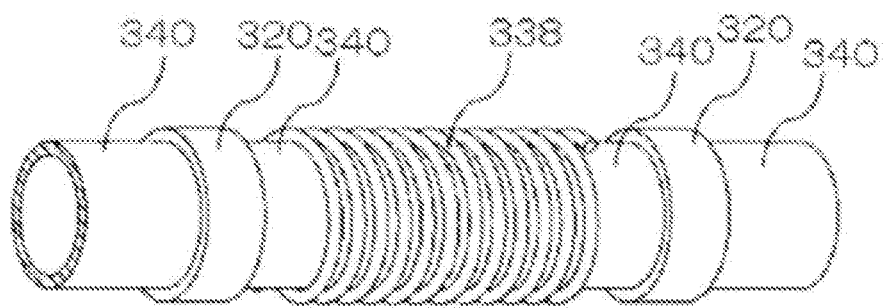

A fifth embodiment is still another embodiment of the composite electrode type intracardiac defibrillation catheter unit according to the present invention. The fifth embodiment has the same overall shape as the first embodiment, but differs in the configuration of the defibrillation electrode. FIG. 9A takes out and shows a part of a defibrillation electrode 336 and the EP inspection electrode 320 of the composite electrode type intracardiac defibrillation catheter according to the fifth embodiment. The defibrillation electrode 336 is an electrode wound around the surface of the catheter shaft 310 as in the defibrillation electrode 332 according to the third embodiment.

However, in the present fifth embodiment, a single-wire conductive cable having a circular cross section is densely wound around the surface of the catheter shaft 310, that is, the single-wire conductive cable is wound such that portions thereof are in contact with each other. In this case, according to the above-mentioned Gauss' theorem, the current emission isotopically goes to a space on the opposite side of the catheter shaft 310 and where there is no defibrillation electrode, so that the emission current is larger than in the cylinder-shaped defibrillation electrode shown in the first and second embodiments. Accordingly, the emission current from the defibrillation electrode 336 is larger than in the first embodiment using the defibrillation electrode 330 and the second embodiment using the defibrillation electrodes 330a and 330b.

A single-wire conductive cable having a circular cross section constituting the defibrillation electrode 336 may be formed by drawing a conductive cable embedded inside the catheter shaft 310 to the surface of the catheter shaft 310 and winding it around the catheter shaft 310 from its drawing-out port. With such a configuration, the number of components is reduced, the manufacturing process of the electrode catheter 310 is reduced, and the composite electrode type intracardiac defibrillation catheter unit can be easily manufactured. Note that the EP inspection electrode 320 may be formed by winding a single-wire conductive cable having a circular cross section around the surface of the catheter shaft 310 in a reel or by winding it densely like the defibrillation electrode 336.

Sixth Embodiment

A sixth embodiment is still another embodiment of the composite electrode type intracardiac defibrillation catheter unit according to the present invention. The sixth embodiment has the same overall shape as the first embodiment, but differs in the configuration of the defibrillation electrode. FIG. 9B takes out and shows a part of a defibrillation electrode 338 and the EP inspection electrode 320 of the composite electrode type intracardiac defibrillation catheter according to the sixth embodiment. The defibrillation electrode 338 is an electrode wound around the surface of the catheter shaft 310 as in the defibrillation electrode 336 according to the fifth embodiment, and a single-wire conductive wire having a circular cross section is roughly wound, that is, the single-wire conductive wire is wound around the surface of the catheter shaft 310 so as to be non-contact.

The defibrillation electrode 336 according to the fifth embodiment is densely wound, but in the sixth embodiment, the defibrillation electrode 338 is roughly wound. Because of the rough winding, the termination effect is larger than that in the dense winding, but the number of windings is reduced compared to the dense winding. However, the emission current of the roughly wound spiral-shaped defibrillation electrode 338 is larger than that of the first embodiment using the defibrillation electrode 330 and that of the second embodiment using the defibrillation electrodes 330a and 330b.

A single-wire conductive cable having a circular cross section constituting the defibrillation electrode 338 may be formed by drawing a conductive cable embedded inside the catheter shaft 310 to the surface of the catheter shaft 310 and winding it around the catheter shaft 310 from its drawing-out port. With such a configuration, the number of components is reduced, the manufacturing process of the electrode catheter is reduced, and the composite electrode type intracardiac defibrillation catheter and the composite electrode type intracardiac defibrillation catheter unit can be easily manufactured. It should be noted that the EP inspection electrode 320 may be formed by winding a single-wire conductive cable having a circular cross section on the surface of the catheter shaft 310 in a reel or by winding it densely like the defibrillation electrode 338.

Seventh Embodiment

Figure 10:
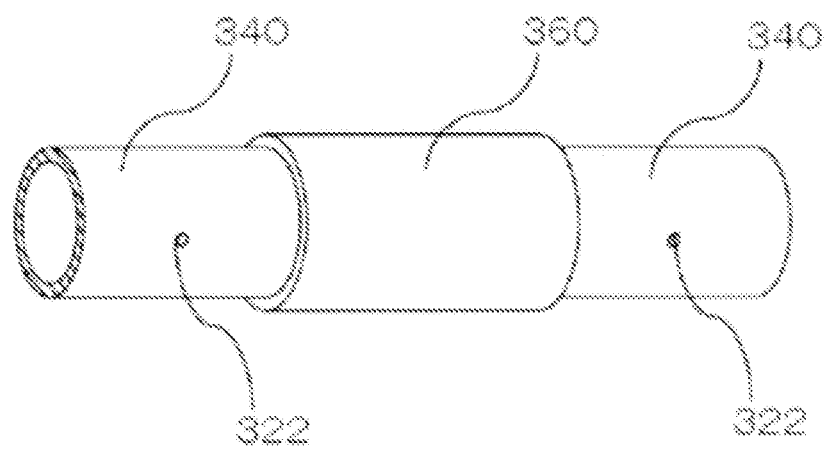
FIG. 10 is a perspective view showing main parts of an EP inspection electrode and a defibrillation electrode when an EP inspection electrode according to a seventh embodiment is constituted by a cut surface of a circular single wire cable.

A seventh embodiment is still another embodiment of the composite electrode type intracardiac defibrillation catheter unit according to the present invention. The seventh embodiment has the same overall shape as the first embodiment, but differs in the configuration of the EP inspection electrode. FIG. 10 takes out and shows a part of the defibrillation electrode 330 and an EP inspection electrode 322 of the composite electrode type intracardiac defibrillation catheter according to the seventh embodiment. The defibrillation electrode 360 has a cylindrical shape similar to the defibrillation electrode 330 according to the first embodiment. On the other hand, the EP inspection electrode 322 is formed by drawing a conductive cable embedded inside the catheter shaft 310 to the surface of the catheter shaft 310 and cutting its drawing-out port as it is, and exposing it on a surface of the catheter shaft 310 so as to have almost a same surface as the surface. The formation may be performed by grinding or polishing the cut surface of the conductive cable. With such a configuration, the number of components is reduced, the manufacturing process of the electrode catheter is reduced, and the composite electrode type intracardiac defibrillation catheter and the composite electrode type intracardiac defibrillation catheter unit can be easily manufactured.

The EP inspection electrode 322 in the seventh embodiment is a so-called point electrode, and has the directionality of inspection depending on the expected angle due to the rotation of the composite electrode type intracardiac defibrillation catheter unit. Therefore, by rotation of the composite electrode type intracardiac defibrillation catheter unit, the difference in the fibrillation causing site can be understood. For example, in the abnormal excitation of cells in the atrioventricular node and sinoatrial node, the difference in detection of electrical signals caused by abnormal excitation of cells due to the expected angle of the EP inspection electrode 322, which is a point electrode due to the narrow generation site, appears greatly with respect to the rotation direction of the composite electrode type intracardiac defibrillation catheter unit.

On the other hand, abnormal excitement of cells in the atrioventricle, and further in the atrial myocytes and ventricular myocytes, is greatly directed to the blood space, and thus the difference in detection of electrical signals caused by abnormal excitation of cells due to the rotation of the composite electrode type intracardiac defibrillation catheter unit does not appear greatly. From such a difference in detection of electric signals, it is possible to determine a site where abnormal excitation or fibrillation of cells occurs. The defibrillation electrode 360 may have any shape among a single cylindrical shape as shown in FIG. 10, a divided cylindrical shape, a spiral shape, and a circular cross-section single-wire conductive cable shown in the second to seventh embodiments.

Eighth Embodiment

Figure 11:
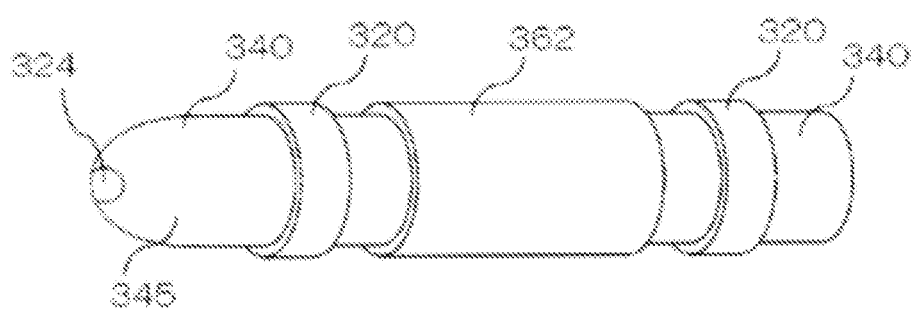
FIG. 11 is a perspective view showing a main part of an electrode catheter according to an eighth embodiment in which a tip EP inspection electrode is also provided on a catheter shaft head which is a front end portion of the electrode catheter.

An eighth embodiment is still another embodiment of the composite electrode type intracardiac defibrillation catheter unit according to the present invention. The eighth embodiment has the same overall shape as the first embodiment, but differs in the configuration of the EP inspection electrode. FIG. 11 shows a main part including the catheter shaft head 345 that is a tip portion of the composite electrode type intracardiac defibrillation catheter according to the eighth embodiment.

In addition to the EP inspection electrode 320, the catheter shaft head 345 is further provided with a tip EP inspection electrode 324 for EP detection. Since the tip EP inspection electrode 324 is not a plane but a point detection, it becomes easy to detect the excitement of the cells in the His bundle. In order to detect the excitement of the cells, the voltage between the tip EP inspection electrode 324 and one or more other EP inspection electrodes 320 is measured. A defibrillation electrode 362 may have any shape among a single cylindrical shape as shown in FIG. 11, a divided cylindrical shape, a spiral shape, and a circular cross-section single-wire conductive cable shown in the second to seventh embodiments.

In the first to eighth embodiments, the defibrillation electrodes 330 (331), 330a (331a), 330b (331b), 332 (333), 334 (335), 336 (337), 338 (339), 360 (361), 362 (363), and the EP inspection electrode 320 (321) (except for the EP inspection electrode 322 of the seventh embodiment and the tip EP inspection electrode 324 of the eighth embodiment) are all formed so as to surround the surface of the catheter shaft 310. However, these electrodes in the first to eighth embodiments may be formed so as to be half buried in the surface of the catheter shaft 310. Also, the EP inspection electrodes 320, 321 and the defibrillation electrodes 330 (331), 330a (331a), 330b (331b), 332 (333), 334 (335), 336 (337), 338 (339), 360 (361), 362 (363) in the first to eighth embodiments may be buried in the surface of the catheter shaft 310, and the surfaces of these EP inspection electrode 320 (321) and defibrillation electrodes 330 (331), 330a (331a), 330b (331b), 332 (333), 334 (335), 336 (337), 338 (339), 360 (361), and 362 (363) may coincide with the surface of the catheter shaft 310. The fact that the surface of the electrode catheter 310 is the same surface facilitates the smooth percutaneous entry of the electrode catheter into the heart chamber and coronary vein during the operation, and therefore the insides of the heart chamber and vein are less damaged, which is preferable.

Further, as described above, with the structure in which the defibrillation electrodes 330 (331), 330a (331a), 330b (331b), 332 (333), 334 (335), 336 (337), 338 (339), 360 (361), 362 (363) and the EP inspection electrode 320 (321) are half-buried or wholly buried in the surface of the catheter shaft 310, blood on the surface of the electrode catheter and thrombus are hardly adhered, and disposal or disinfection of the electrode catheter after using the composite electrode type intracardiac defibrillation catheter 400 is facilitated.

The composite electrode type intracardiac defibrillation catheter 400 in the first to eighth embodiments may include various defibrillation electrodes 330 (331), 330a (331a), 330b (331b), 332 (333), 334 (335), 336 (337), 338 (339), 360 (361), 362 (363), EP inspection electrodes 320 (321), 322, and tip EP inspection electrode 324 provided on the surface of the catheter shaft 310 by mutual combination other than the combinations shown in the first to eighth embodiments.

A pull wire (not shown) is assembled to the composite electrode type intracardiac defibrillation catheter 400 in the first to eighth embodiments, or to the composite electrode type intracardiac defibrillation catheter constituted by mutual combination other than the combinations shown in the first to eighth embodiments, and a composite electrode type intracardiac defibrillation catheter unit including the pull wire may be constituted. In this case, for example, in the composite electrode type intracardiac defibrillation catheter unit 500, one end of the pull wire is connected inside the catheter shaft head 345, the whole is embedded in the catheter shaft 310, and the other end is drawn to the terminal connecting part and attached to the composite electrode type intracardiac defibrillation catheter unit 500. With such a structure, the tip portion of the electrode catheter is bent by pulling the pull wire forward, in other words, by the tip deflection operation, and the electrode catheter can be easily made to enter the bent portion in the venous blood vessel or the heart chamber.

Ninth Embodiment

One of the objects of the present invention is to allow sufficient current emission from the defibrillation electrode even with a relatively low defibrillation electric shock. However, a defibrillation electrode according to the defibrillation electrodes 330 (331), 330a (331a), 330b (331b), 332 (333), 334 (335), 336 (337), 338 (339), 360 (361), 362 (363) and an EP inspection electrode according to the EP inspection electrodes 320 (321) and 322 are spatially divided from the defibrillation electrode and used independently.

Therefore, the defibrillation current is released only from the defibrillation electrode. Therefore, the magnitude of the defibrillation current is determined by the number, shape and area of the defibrillation electrodes. Therefore, in the ninth embodiment, after the EP inspection electrode is temporally divided, and an abnormal excitation site or the like such as in the heart chamber is detected, when a defibrillation current caused by a defibrillation electric shock is made to flow through the site, the defibrillation electric shock is applied also to the EP inspection electrodes 320 (321) and 322 so that the defibrillation current flows. That is, when a defibrillation current is made to flow, the EP inspection electrode 320 (321) is used as a defibrillation electrode.

Figure 12:
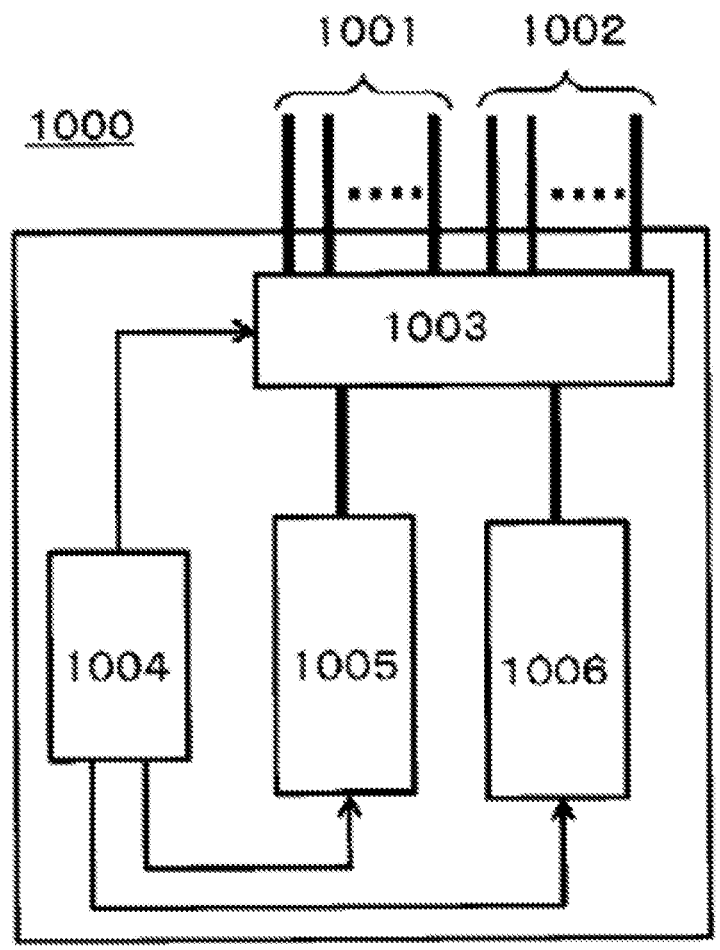
FIG. 12 is a diagram showing a configuration of a control power supply unit used in the composite electrode type intracardiac defibrillation catheter unit according to the present invention.

In order to time-divide the EP inspection electrode and use it as an EP inspection electrode and further also as a defibrillation electrode in this way, a time-division control device is required. FIG. 12 shows a control power supply unit 1000 having a time division function according to the ninth embodiment. The EP inspection electrodes 320 (321) and 322 and the defibrillation electrodes 330 (331), 330a (331a), 330b (331b), 332 (333), 334 (335), 336 (337), 338 (339), 360 (361), and 362 (363) are connected to correspond to a first electric cable 1001 and a second electric cable 1002 which are connected to the control power supply unit 1000, respectively. The first electric cable 1001 and the second electric cable 1002 are connected to a relay 1003.

The relay 1003 is further connected to a high-voltage generating power source 1005 and an EP inspection measuring instrument 1006. The high-voltage generating power source 1005 generates defibrillation electric shock necessary for defibrillation and accumulates and maintains the voltage until applying the voltage to the defibrillation electrodes 330 (331), 330a (331a), 330b (331b), 332 (333), 334 (335), 336 (337), 338 (339), 360 (361), 362 (363) and the EP inspection electrodes 320 (321), 322.

On the other hand, the EP inspection measuring instrument 1006 converts a voltage (intracardiac signal), which the EP inspection electrodes 320 (321) and 322 have detected by contacting a fibrillation occurring site or a site where a signal caused by fibrillation is generated in the heart, chamber, into a signal for measurement, and has a display function that the operator can visually perceive the signal and a function of storing the intracardiac signal as data. Operations and functions of the high-voltage generating power source 1006 and the EP inspection measuring instrument 1006 are controlled by the controller 1004.

That is, the controller 1004 controls the generation of the defibrillation electric shock of the high-voltage generating power source 1005, its maintenance, stop and application of the defibrillation electric shock to the relay 1003, controls the operation of the EP inspection measuring instrument 1006, selects connection/non-connection of the first electric cable 1001 and the EP inspection measuring instrument 1006 by the control of the relay 1003, and selects connection/non-connection of the first electric cable 1001 and the high-voltage generating power source 1005 by the control of the relay 1003. On the other hand, the second electric cable 1002 is always connected to the high-voltage generating power source 1005.

Figure 13:
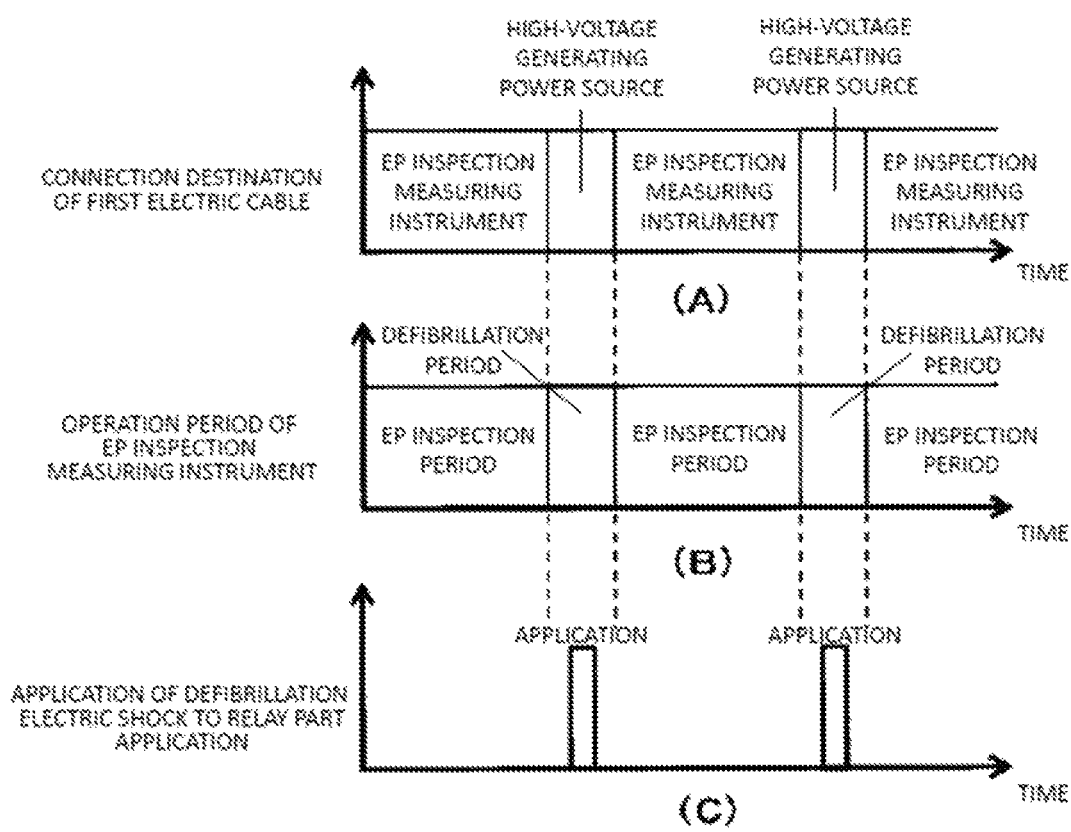
FIG. 13 is a diagram showing the operation of the control power supply unit when used in the composite electrode type intracardiac defibrillation catheter unit according to the present invention.

The control of the controller 1004 selects connection/non-connection of the first electric cable 1001 and the EP inspection measuring instrument 1006, and selects connection/non-connection of the first electric cable 1001 and the high-voltage generating power source 1005. As a result, the connection partner of the second electric cable 1002 is as shown in FIG. 13(A). That is, when the composite electrode type intracardiac defibrillation catheter unit 500 searches for an abnormal excitation site such as in the heart chamber in the heart chamber or the like, the first electric cable 1001 is connected to the EP inspection measuring instrument 1006. When the defibrillation electric shock is applied to the site for defibrillation, the first electric cable 1001 is connected to the high-voltage generating power source 1005. On the other hand, for the EP inspection measuring instrument 1006, the EP inspection period and the defibrillation period are selected as shown in the temporal change chart of FIG. 13(B) by the control of the controller 1004.

In order to apply the defibrillation electric shock to the defibrillation electrodes 330 (331), 330a (331a), 330b (331b), 332 (333), 334 (335), 336 (337), 338 (339), 360 (361), 362 (363) and the EP inspection electrodes 320 (321) and 322, as shown in FIGS. 13(B) and 13(C), the controller 1004 applies a defibrillation electric shock pulse from the high-voltage generating power source 1005 in the defibrillation period during which the first electric cable 1001 is connected to the high-voltage generating power source 1005.

By the operation of the controller 1004, the EP inspection electrodes 320 (321) and 322 can be used both when an abnormal excitement site such as in the heart chamber or the like is searched for and when the defibrillation electric shock is applied to the site for defibrillation. In defibrillation, since the defibrillation electrodes 330 (331), 330a (331a), 330b (331b), 332 (333), 334 (335), 336 (337), 338 (339), 360 (361), 362 (363) and the EP inspection electrodes 320 (321) and 322 can be used, the discharge current increases. Therefore, the applied voltage can be lowered correspondingly, and the composite electrode type fibrillation catheter 400 that is less likely to cause dielectric breakdown can be realized.

Figure 14:
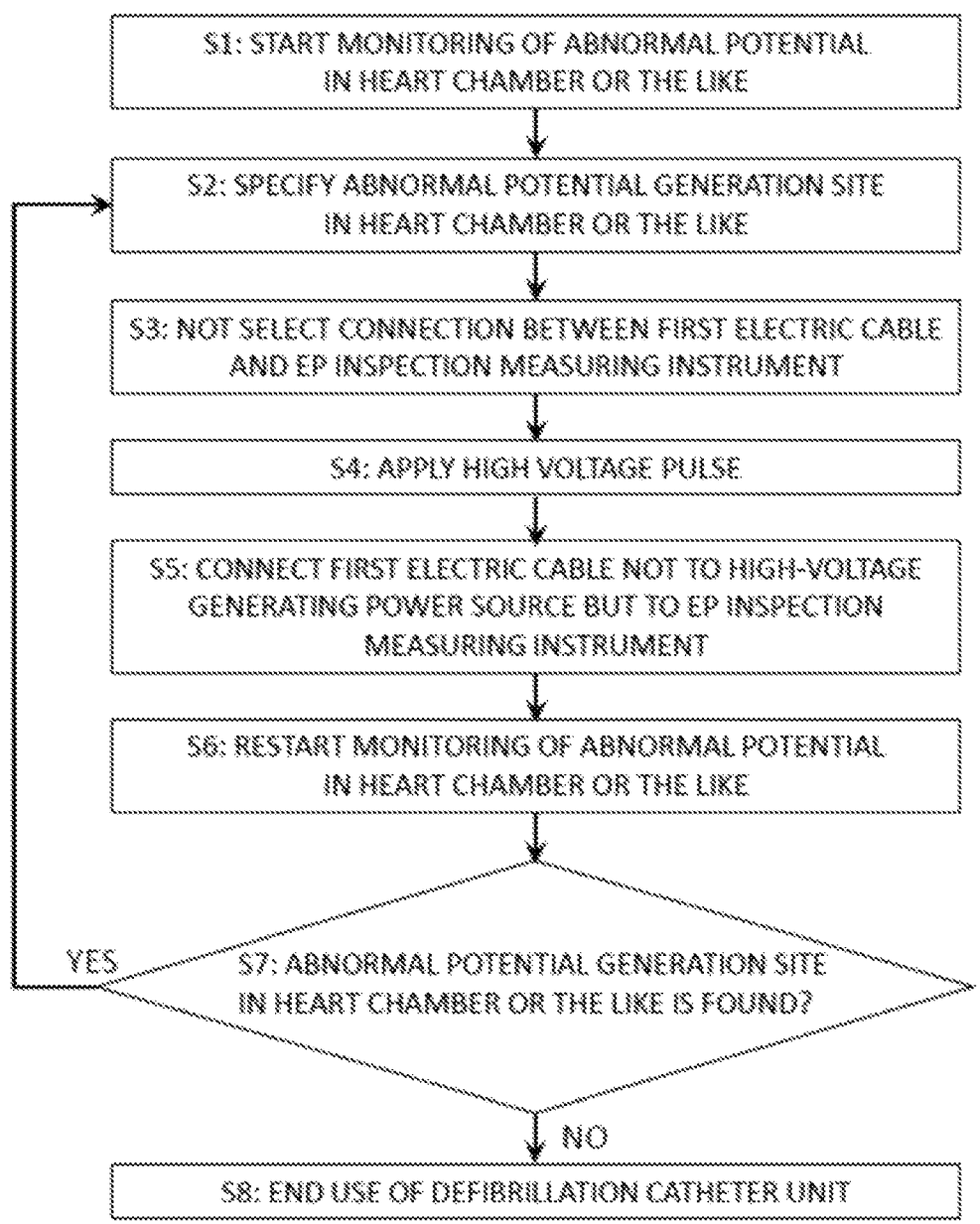
FIG. 14 is a flowchart showing a procedure for using the composite electrode type intracardiac defibrillation catheter unit according to the present invention.

FIG. 14 is a flowchart showing a procedure for using the composite electrode type intracardiac defibrillation catheter unit 500 according to the present invention using the control power supply unit 1000 described in the ninth embodiment. That is, monitoring of an abnormal potential of an abnormal excitement site or the like in the heart chamber or the like (hereinafter referred to as "in the heart chamber or the like" for the sake of simplicity) is started (S1). The composite electrode type intracardiac defibrillation catheter unit is moved in the heart chamber or the like, and the abnormal potential generation site is specified (S2). Thereafter, the controller 1004 controls the relay 1003 to select non-connection between the first electric cable 1001 and the EP inspection measuring instrument 1006 and select connection between the first electric cable 1001 and the high-voltage generating power source 1005 (S3). Thereafter, the controller 1004 applies a defibrillation electric shock pulse from the high-voltage generating power source 1005 (S4), and thereby the defibrillation electric shock pulse is applied to the first electric cable 1001 and the second electric cable 1002. Next, the controller 1004 controls the relay 1003 to select non-connection between the first electric cable 1001 and the high-voltage generating power source 1005 and select connection between the first electric cable 1001 and the EP inspection measuring instrument 1006 (S5). Again, monitoring of abnormal potential in the heart chamber or the like is started (S6). Thereafter, the composite electrode type intracardiac defibrillation catheter unit 500 is moved in the heart chamber or the like to search for an abnormal potential generation site and determine the result (S7). That is, if an abnormal potential generation site is found, the process returns to step S2, and if no abnormal potential generation site is found, the process proceeds to step S8 and ends the use of the composite electrode type intracardiac defibrillation catheter unit 500 (S8).

The composite electrode type intracardiac defibrillation catheter unit 500 is operated and used according to the above procedure.

REFERENCE SIGNS LIST 10, 310 catheter shaft
11, 340, 380 inter-electrode gap
20 EP inspection electrode
20G EP inspection electrode group
320, 321, 322 EP inspection electrode (first electrode)
320G, 321G EP inspection electrode group (first electrode group)
30, 31a, 31b defibrillation electrode
31G, 32G defibrillation electrode group
330, 331, 330a, 331a, 330b, 331b, 332, 333, 334, 335, 336, 337, 338, 339, 360, 361, 362, 363 defibrillation electrode (second electrode)
330G, 331G defibrillation electrode group (second electrode group)
324 EP inspection electrode (third electrode)
21, 326 grip part
23 connection termination part
24, 324 strain relief
25 connector pin
26 latch mechanism
45, 345 catheter shaft head
50 handle
100 electrode catheter
200 intracardiac defibrillation catheter unit
323-1, 323-2 connector
324 tip EP inspection electrode
325-1, 325-2 external wire
345 catheter shaft head
400 composite electrode type intracardiac defibrillation catheter
500 composite electrode type intracardiac defibrillation catheter unit
1000 control power supply unit
1001 first electric cable
1002 second electric cable
1003 relay
1004 controller 1005 high-voltage generating power source
1006 EP inspection measuring instrument

The invention claimed is:

1. A composite electrode intracardiac defibrillation catheter, comprising:
a flexible catheter shaft made of an insulating member;
a first electrode group on a surface of the flexible catheter shaft;
a second electrode group on the surface of the flexible catheter shaft;
a conductive cable connected to the first electrode group and the second electrode group, and wired inside the flexible catheter shaft;
a strain relief;
a gripping part;
a first external electric wire;
a second external electric wire;
a first connector; and
a second connector,
wherein:
the first electrode group includes at least two first electrodes for detecting an electrophysiological electrical signal of a site or a cell group in a heart chamber;
the second electrode group includes at least one second electrode located between an adjacent pair of the at least two first electrodes for causing an electric current by a high-voltage defibrillation electric shock for defibrillation to flow in a contact site in the heart chamber or a contact site in a vein;
a conductive length of a surface of the at least one second electrode in a longitudinal direction of the flexible catheter shaft is longer than a conductive length of each of the at least two first electrodes;
the conductive cable is configured to be connected to a control power supply unit via the strain relief and the gripping part, through: (i) the first external electric wire and the first connector; or (ii) the second external wire and the second connector;
the second electrode group is one of a plurality of defibrillation electrode groups;
a first portion of the conductive cable is connected to a first of the plurality of defibrillation electrode groups;
a second portion of the conductive cable is connected to a second of the plurality of defibrillation electrode groups; and
the first portion of the conductive cable and the second portion of the conductive cable are electrically separated from each other for reducing dielectric breakdown inside the flexible catheter shaft.

2. The composite electrode intracardiac defibrillation catheter according to claim 1, wherein a combination of the first electrode group and the second electrode group is provided at each of two places on the flexible catheter shaft.

3. The composite electrode intracardiac defibrillation catheter according to claim 1, further comprising a third electrode which is an electrophysiological inspection electrode independently formed at a tip portion of the flexible catheter shaft and connected to the conductive cable.

4. The composite electrode intracardiac defibrillation catheter according to claim 1, wherein each of the at least two first electrodes has an annular shape or a cylindrical shape.

5. The composite electrode intracardiac defibrillation catheter according to claim 1, wherein each of the at least two first electrodes is a conductive cable having a circular cross section formed so as to be exposed to the surface of the flexible catheter shaft and to be continuous with the surface of the flexible catheter shaft.

6. The composite electrode intracardiac defibrillation catheter according to claim 5, wherein each of the at least two first electrodes is made of the same material as the conductive cable.

7. The composite electrode intracardiac defibrillation electrode catheter according to claim 5, wherein half of the at least one second electrode is embedded in the surface of the flexible catheter shaft.

8. The composite electrode intracardiac defibrillation catheter according to claim 1, wherein each of the at least two first electrodes is a conductive portion formed by winding a conductive cable having a circular cross section around the flexible catheter shaft.

9. The composite electrode intracardiac defibrillation catheter according to claim 1, wherein the at least one second electrode has a cylindrical shape.

10. The composite electrode intracardiac defibrillation catheter according to claim 1, wherein the at least one second electrode has a cylindrical shape as a whole and has a spiral shape in the longitudinal direction of the flexible catheter shaft.

11. The composite electrode intracardiac defibrillation catheter according to claim 10, wherein the spiral shape of the at least one second electrode has a dense spiral interval.

12. The composite electrode intracardiac defibrillation catheter according to claim 10, wherein the spiral shape of the at least one second electrode has a rough spiral interval.

13. The composite electrode intracardiac defibrillation catheter according to claim 1, wherein the at least one second electrode is a conductive portion formed by winding a conductive cable having a circular cross section around the flexible catheter shaft.

14. The composite electrode intracardiac defibrillation catheter according to claim 13, wherein the conductive cable is densely wound around the flexible catheter shaft.

15. The composite electrode intracardiac defibrillation catheter according to claim 13, wherein the conductive cable is roughly wound around the flexible catheter shaft.

16. The composite electrode intracardiac defibrillation catheter according to claim 13, wherein the at least one second electrode is made of the same material as the conductive cable.

17. The composite electrode intracardiac defibrillation catheter according to claim 1, wherein half of each of the at least two first electrodes and the at least one second electrode are embedded in the surface of the flexible catheter shaft.

18. The composite electrode intracardiac defibrillation catheter according to claim 1, wherein the at least two first electrodes and the at least one second electrode are embedded in the surface of the flexible catheter shaft, and surfaces of the at least two first electrodes and the surface of the at least one second electrode are flush with the surface of the flexible catheter shaft.

19. The composite electrode intracardiac defibrillation catheter according to claim 1, wherein the flexible catheter shaft is a hollow tube or a porous tube.

20. The composite electrode intracardiac defibrillation catheter according to claim 1, wherein an inner wall layer of the flexible catheter shaft is lined with a braid of a low hardness nylon elastomer, a high hardness nylon elastomer, or a stainless steel element wire.

21. The composite electrode intracardiac defibrillation catheter according to claim 1, wherein the flexible catheter shaft is a porous tube, and an inner wall of the porous tube is lined with a layer made of fluororesin.

22. The composite electrode intracardiac defibrillation catheter according to claim 1, wherein a coating of the conductive cable is made of any one of polyimide resin, polyamide resin, and polyamideimide resin, and has a thickness of 20 μm to 40 μm.

23. A composite electrode intracardiac defibrillation catheter unit, comprising:
   the composite electrode intracardiac defibrillation catheter according to claim 1;
   a terminal connecting part at one end of the composite electrode intracardiac defibrillation catheter; and
   a conductive connector pin at the terminal connecting part, the conductive connector pin being electrically connected to the conductive cable.

24. The composite electrode intracardiac defibrillation catheter unit according to claim 23, wherein:
   the composite electrode intracardiac defibrillation catheter further includes a pull wire that is connected to an inside of a tip portion of the flexible catheter shaft, is embedded inside the flexible catheter shaft, and has one end drawn out to the terminal connecting part.

* * * * *